US00PP18459P3

(12) United States Plant Patent
Brooks

(10) Patent No.: US PP18,459 P3
(45) Date of Patent: Jan. 22, 2008

(54) AVOCADO TREE NAMED 'WHEELING'

(50) Latin Name: *Persea americana*
Varietal Denomination: Wheeling

(76) Inventor: Neal Palmer Brooks, P.O. Box 900160, Homestead, FL (US) 33090-0160

( * ) Notice: Subject to any disclaimer, the term of this patent is extended or adjusted under 35 U.S.C. 154(b) by 225 days.

(21) Appl. No.: 11/205,815

(22) Filed: Aug. 17, 2005

(65) Prior Publication Data

US 2007/0044183 P1 Feb. 22, 2007

(51) Int. Cl.
*A01H 5/00* (2006.01)

(52) U.S. Cl. ..... Plt./200

(58) Field of Classification Search ..... Plt./200
See application file for complete search history.

*Primary Examiner*—Kent Bell
(74) *Attorney, Agent, or Firm*—Michael C. Cesarano; Feldman Gale P.A.

(57) ABSTRACT

The Wheeling' avocado, which is a result of cross-pollination of the 'Monroe' and the 'Brooks Late' varieties, is of medium size, average 12–16 ounces and being about 4.75 inches in length, and has overall good eating qualities. The fruit matures and can be picked in February to early March. The fruit is an ovate berry that has a hard shelled, smooth textured, exocarp that is dark green.

4 Drawing Sheets

Scientific Name: *Persea americana* Mille var. 'Wheeling'.

BACKGROUND OF THE INVENTION

During the decades of the '70's, '80's, and extending into the '90's, attempts were made to grow avocado plants in an area of Southwest Florida near the town of Immokalee. Cold winter weather and repeated freezes eventually overcome most of the attempts by killing the trees or their fruit before they could reach maturity. Two varieties, however, were able to reach maturity. These were the 'Monroe', a type "B" flower, and the 'Brooks Late', a type "A" flower. Flowers on type "A" trees open as female in the morning of the first day and as male the afternoon of the following day. On type "B" trees the flowers open as female in the afternoon on the first day and as male on in the morning of the following day. Hence, the flower "types" are female: male complementary with respect to their periods of opening.

The 'Monroe' was larger, and could be used by customers who want large slices. The 'Brooks Late' was the latest maturing, but was too small for commercial sales. Cross pollination of these two varieties was attempted in an effort to produce an avocado having the best characteristics of each.

Cultivar 'Monroe' was used as male and 'Brooks Late' as female in 1999 in Immokalee, Fla. Several hundred cross-pollinated fruits were harvested and the seeds were planted in a lime stone soil in 1999 in Homestead, Fla. From those seeds, plants that did not show healthy growth, or those which showed signs of being overly susceptible to the scap fungus disease were discarded. Of the remaining plants, only one plant of the 'Wheeling' variety not only showed tolerance to scab but also matured in February to early March, and shows promise for commercial development.

BRIEF SUMMARY OF THE INVENTION

All color descriptions employ the Munsell Color Charts for Plant Tissues, Gretag Macbeth LLC, 617 Little Britain Road, New Windsor, N.Y. 12553-6148. The complete Munsell notation for any chromatic color is written: Hue (Value/Chroma).

Asexual propagation using branches was attained in 2002 in Homestead, Fla. when the plant was 3 years old.

The tree is now five years old. It differs from other late varieties and its parents on the lateness of the maturity of the fruit. 'Wheeling' presents more resistance than other late varieties do to *Cerospora purpurea* and *Colletotrichum gloeosporoides* pathogens. This variety's tolerance to frost is stronger than other late cultivars such as 'Monroe'.

DETAILED BOTANICAL DESCRIPTION

Figure 1:
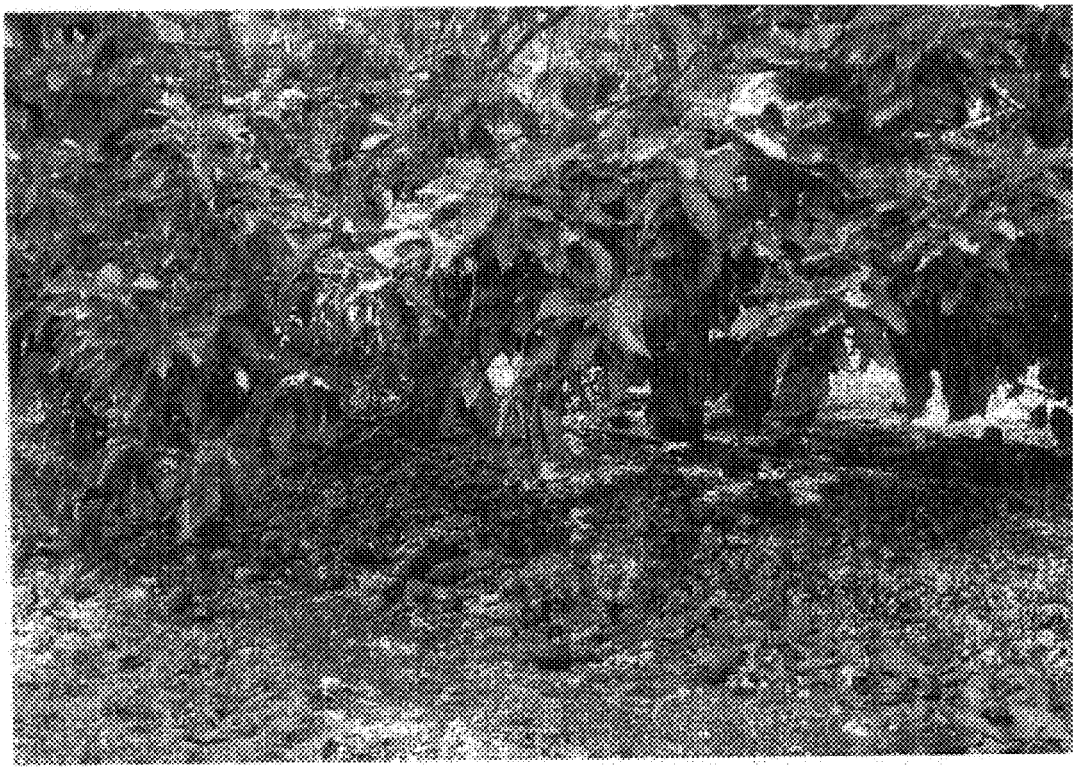
FIG. 1 shows leaf detail and a portion of the trunk at a lower portion of the avocado tree.

The tree presents a vigorous upright growth with a spread of 13 feet and 20 feet high; as shown in FIGS. 1, 3, 4, 6 and 8. As included in FIG. 1, the diameter of the main trunk is 6–8 inches (obtained at 16 inches above the ground) tapering as it extends straight and upward to the pinnacle of the tree, pendant branches of 2–3 inches in diameter split off of the vertical trunk, these in turn giving way to smaller and smaller branches growing in pendant fashion. One year of wood averages one inch in diameter.

The bark on the trunk and branches is light in color 2.5 Y (6/2). One year old wood is somewhat darker at 7.5 YR (5/2). New shoots average 0.5 inches in diameter and are greenish yellow 2.5GY (8/6).

The foliage is of heavy density near the ground, becoming sparse toward the upper regions of the tree. Leaves are large and dark green, as appears in FIGS. 1, 3, 4, 6 and 8. The leaves are alternate, entire and, pinnately veined. They are elliptic, narrowly acute at the apex and acute at the base. The mature leaves are 7.25 to 12.2 inches in length and from 3.85 to 4.4 inches wide, the observed one in 9.2 inches long and 4.00 inches wide. Leaves are pubescent when young, becoming smooth and leathery when mature. The upper surface of the leaf exhibits a range of dark green from 7.5 CV (4/3 to 4/4). The underside of the leaf ranges from 5 GY (5/4 to 6/4). Leaf veins are a greenish yellow color of 2.5 GY (7/8). The petioles are 1.4 to 1.6 inches long and 0.125 inches in diameter; the observed one was 1.6 inches long and 0.125 inches wide. The petioles are 2.5 GY (7/6). The leaves are not fragrant when crushed.

Multiple flowers on axillary panicles are borne in a pseudoterminal position and the central axis of the inflorescence terminates in a shoot. Flowers are perfect, with 12 stamens, 9 of which are functional, each having 4 pollen chambers. The single pistil has one carpel with one ovule. The flowers are 0.375 to 0.5 inch in diameter. The lack petals but have 2 whorls of 3 perianth lobes, and are pubescent. The color of the lobes and the pistil is light green 2.5 GY (8/4), the sepals are darker at 2.5 GY (7/6), and the anthers are yellow 2.5 Y (8/10). The flowers are not fragrant. The tree blooms in April and the blooms are of the B type. Fruit matures and can be picked in March of the following year.

Figure 5:
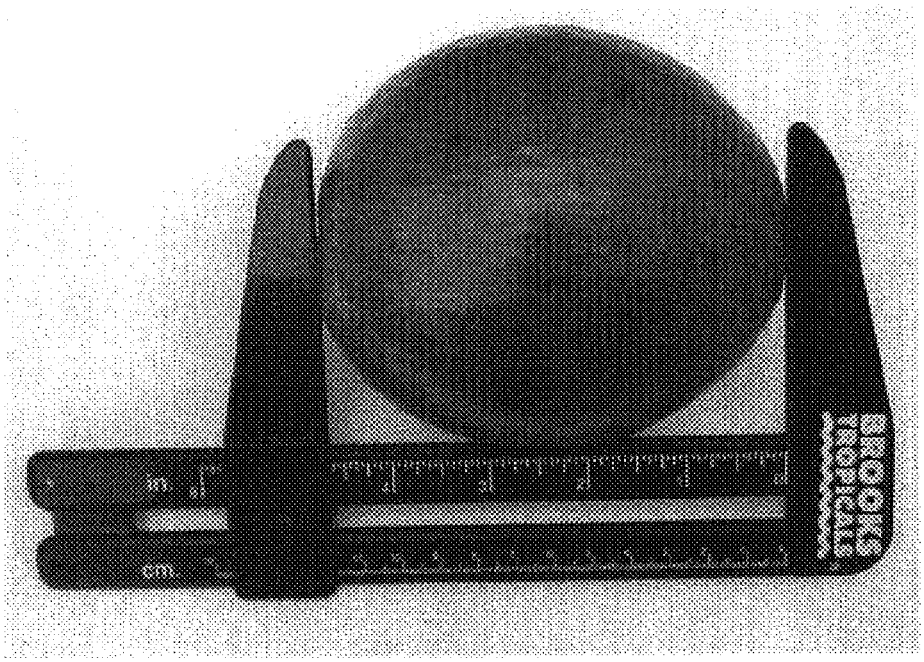
FIG. 5 shows the scale in inches of a typical fruit of the tree measured against a ruler.
Figure 6:
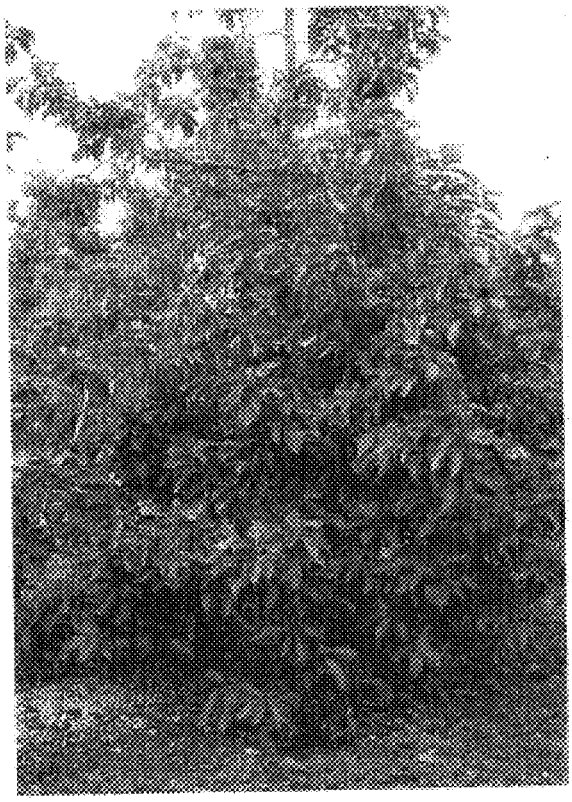
FIG. 6 shows the sparse foliage near the upper portion of the avocado tree.

FIG. 5 shows the outside of the fruit, which is an ovate berry that matures in in February to early March. It has a thick (1/16 inch) hard shelled exocarp, which is smooth textured, and dark green 5GY (4/6). The fruit weighs 12–16 ounces and averages 4.75 inches in length, as shown in FIG. 5.

Figure 2:
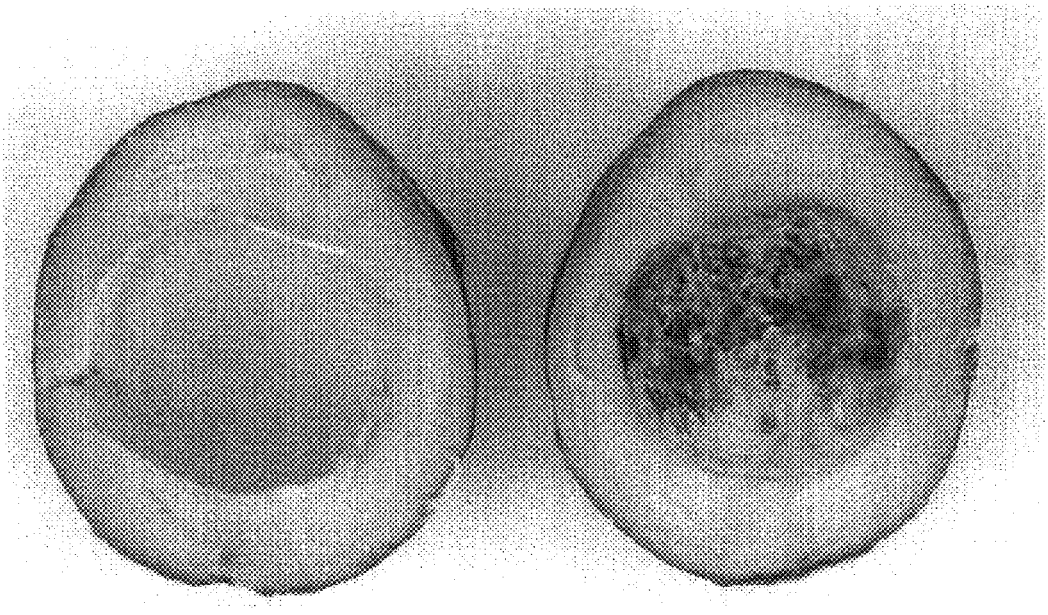
FIG. 2 shows the color and internal configuration of the fruit and the seed.
Figure 3:
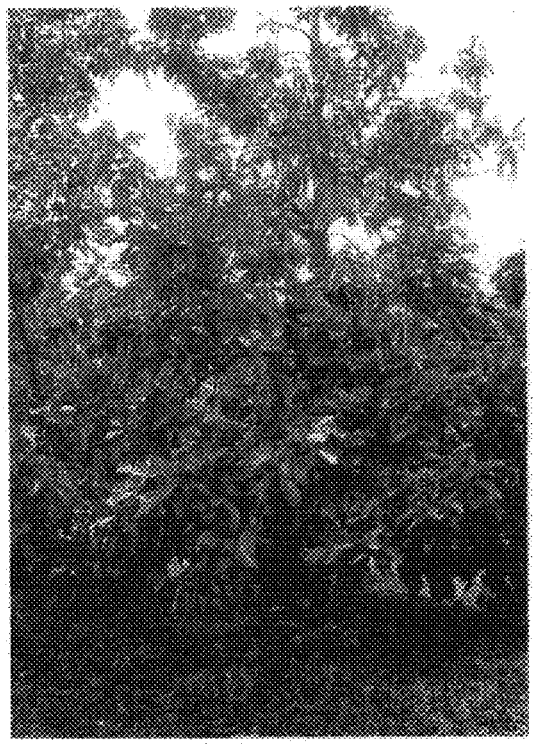
FIG. 3 shows the middle and upper portion of the avocado tree.
Figure 4:
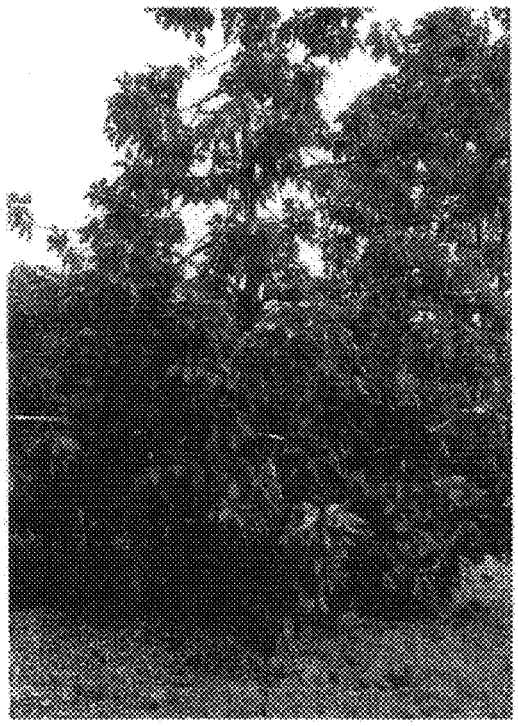
FIG. 4 shows an alternative view of the middle and upper portions of the avocado tree.
Figure 7:
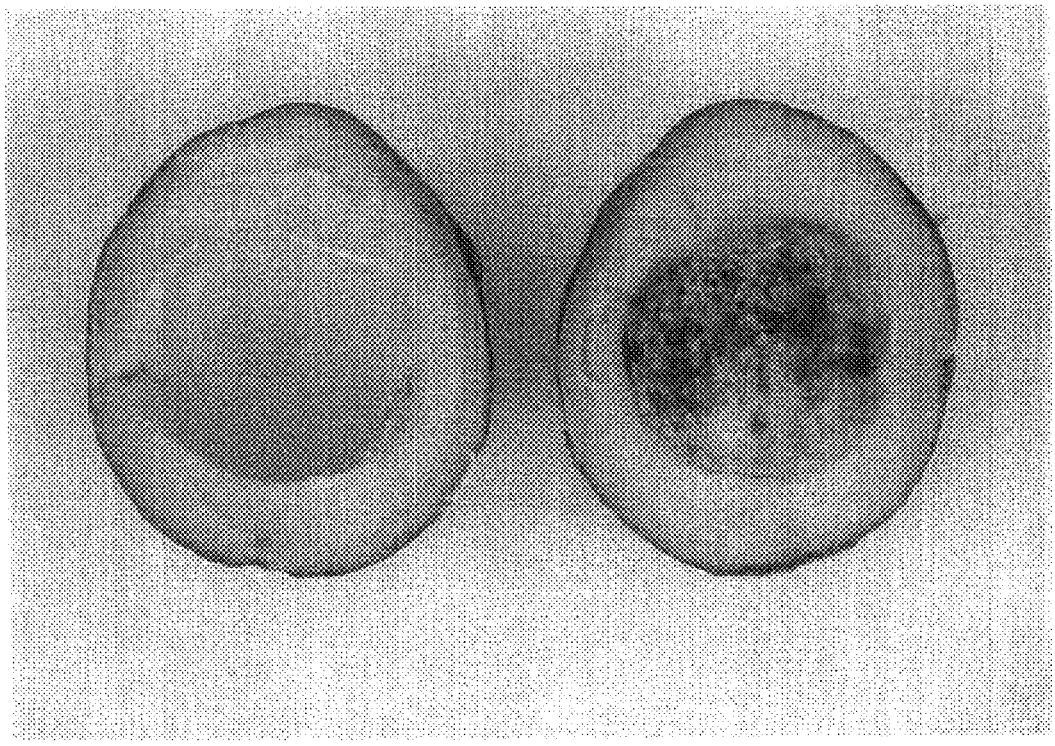
FIG. 7 shows the color and internal configuration of the fruit of FIG. 2 under marginally different lighting conditions.
Figure 8:
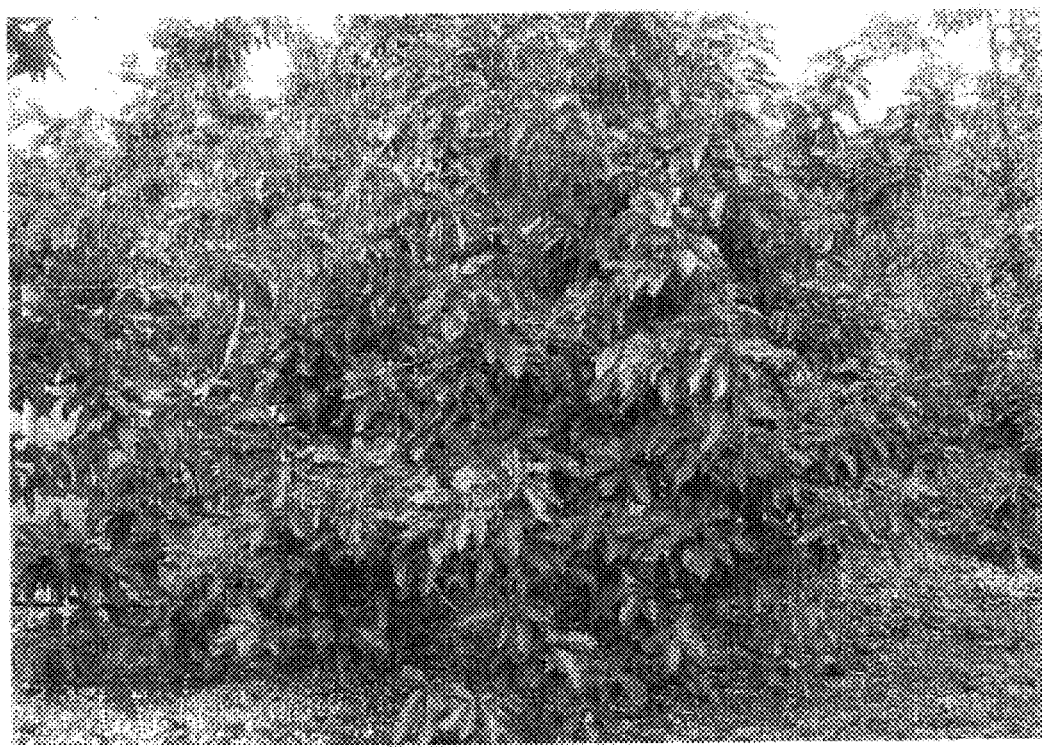
FIG. 8 shows the dense foliage at the lower portion of the avocado tree.

In FIGS. 2 and 7, the interior of the fruit is seen to have a mesocarp color that is green near the shell 5GY (7/8) and yellow near the seed cavity 5Y (8/10). Lenticels are numerous (100–200 per square inch) on the fruit and are light yellowish green in color 2.5 GY (7/10). The fruit also has an excellent flavor.

The seed is tight in the cavity, oblate, and is 1.75 to 2 inches long and is covered by a dark brown endocarp 5 YR (4/4). The Cotyledons are textured and light brown in color 5 YR (6/8).

We claim:

1. A new and distinct variety of avocado tree substantially as described and illustrated and characterized as to novelty by its overall good eating qualities, its medium size and its being ready to be picked in February to early March.

* * * * *